United States Patent [19]

Bray et al.

[11] Patent Number: 5,233,041

[45] Date of Patent: Aug. 3, 1993

[54] SYNTHESIS OF A 3,4-DIHYDROXY-1-CYCLOPENTANYL-PURINONE FROM A 2,3-UNSATURATED-1-CYCLOPENTANYL-PURINONE

[75] Inventors: Brian L. Bray, Graham, N.C.; Maynard E. Lichty, Durham; John J. Partridge, Chapel Hill, all of N.C.; John P. Turnbull, Greenford, United Kingdom

[73] Assignee: Glaxo Group Limited, Greenford, England

[21] Appl. No.: 772,738

[22] Filed: Oct. 7, 1991

[51] Int. Cl.$^5$ .................... C07B 41/02; C07D 473/18
[52] U.S. Cl. ............................................ 544/276
[58] Field of Search .................................. 544/276

[56] References Cited

U.S. PATENT DOCUMENTS 4,621,140 11/1986 Verheyden ............................ 544/276
4,774,325 9/1988 Casadio ................................ 544/265
5,155,112 10/1992 Storer .................................. 544/276

FOREIGN PATENT DOCUMENTS 345076 6/1989 European Pat. Off. .
349242 3/1990 European Pat. Off. .

OTHER PUBLICATIONS

Geiger, Peptides 3, pp. 1–2 (1981).
Behr, Acta Chem Scand B, 31 793–796 (1977).
Huang, Synthesis 1978, pp. 297–299.
Mancuso, A. Activated Dimethyl Sulfoxide: Useful Reagants for Synthesis, Synthesis, pp. 165–185, Mar. 1981.
Schroder, Chemical Reviews, 1980 80, pp. 187–213.
Van Rheem, Tetrahedron Letters, No. 23, pp. 1973–1976 (1976).

Primary Examiner—Mark L. Berch
Attorney, Agent, or Firm—David J. Levy

[57] ABSTRACT

Synthesis of the triol of formula (I) or its amine-protected derivative from a cyclopentene of the formula (II) or its amine-protected derivative:

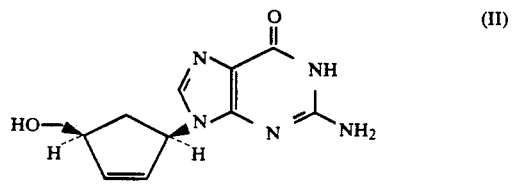

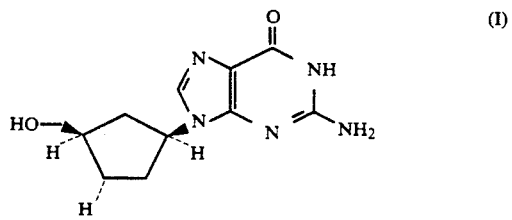

via steps including oxidation to the aldehyde, migration of the double bond, reduction of the aldehyde moiety back to the alcohol grouping and 1,2-cis-dihydroxylation of the double bond.

13 Claims, No Drawings

5,233,041

SYNTHESIS OF A 3,4-DIHYDROXY-1-CYCLOPENTANYLPURI-NONE FROM A 2,3-UNSATURATED-1-CYCLOPENTANYLPURI-NONE

BACKGROUND OF THE INVENTION

Carbocyclic analogues of nucleosides are described in European Patent Application Publication No. 345,076 published Dec. 6, 1989 as being useful as pharmaceuticals in the treatment of viruses, especially Herpetoviridae. A particular compound described is (1'S, 3'S, 4'S)-2-amino-1,9-dihydro-9-[3,4-dihydroxy-3-hydroxymethyl-1-cyclopentyl]-6H-purin-6-one of the following formula (I):

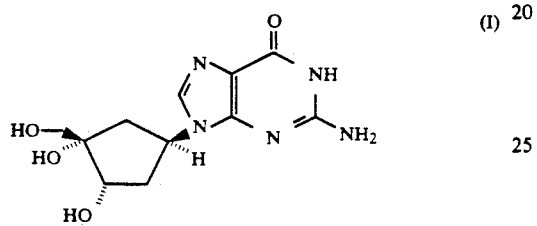

European Patent Application Publication No. 349,242 published Jan. 3, 1990 assigned to the Wellcome Foundation teaches 6-substituted purine carbocyclic nucleosides and Example 45 provides a synthesis of (±)-9-[3-(hydroxymethyl)-3-cyclopenten-1-yl]guanine (racemic compound of formula V).

SUMMARY OF THE INVENTION

Synthetic steps and intermediates involved in the overall reaction scheme of converting carbovir, e.g. (−)-carbovir described in U.K. Patent Application Publication No. 2,217,320A, or (+)-carbovir or (+)-carbovir, of the following formula (II) to the triol of the following formula (I):

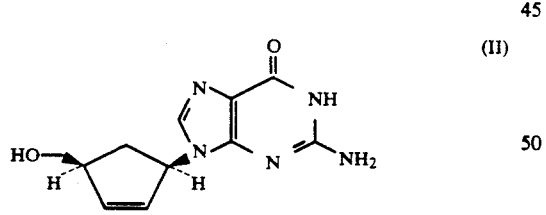

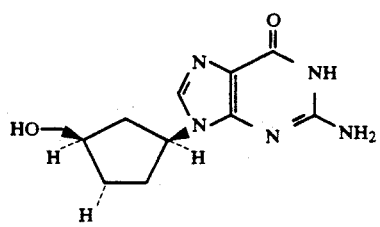

The individual steps include protection of the amino group of (II), oxidation of the alcohol to an aldehyde, migration of the cyclopentene double bond to be in conjugation with the aldehyde, reduction back to an alcohol and cis-hydroxylation of the double bond.

DETAILED DESCRIPTION OF THE INVENTION

The present invention includes the method of synthesizing a triol of the following formula (Ip):

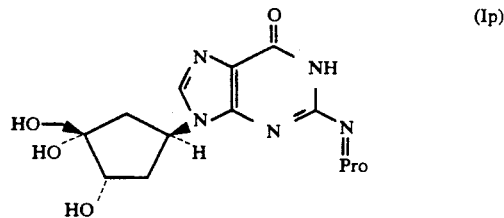

wherein Pro is an amino protecting group, which comprises the steps of:

i) oxidizing a cyclopentene of the following formula (IIp):

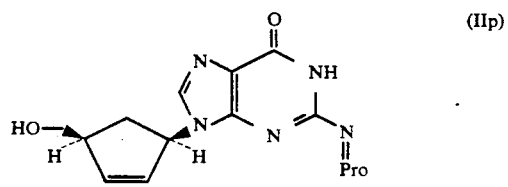

to yield an aldehyde of the following formula (IVp):

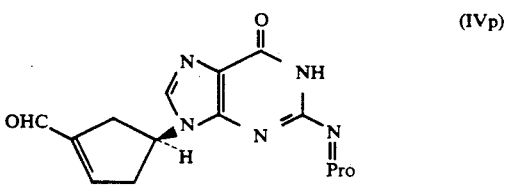

ii) reducing the aldehyde of formula (IVp) to yield the monoalcohol of the following formula (Vp):

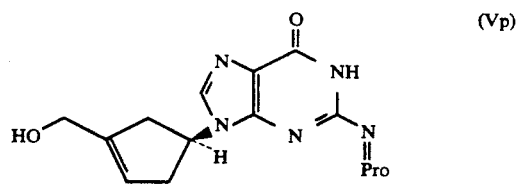

and iii) performing a cis-hydroxylation on the monoalcohol of formula (Vp) to produce the triol of formula (Ip).

Reaction Scheme I which follows sets forth the overall sequence of steps which may be used in carrying out the invention. The compound of formula (II) in the following Reaction Scheme I is reacted with an amine protecting reagent whereby the amino function cannot react with reactants in the subsequent steps, e.g. with $(COCl)_2$. Thus, Pro in formulae (Ip), (IIp), (IIIp), (IVp) and (Vp) represents a moiety bound by a double bond, or 2 moieties bound by 2 single bonds, to the pendant amino nitrogen, e.g.=$CN(CH_3)_2$ or —H and —CHO. Although various amine protecting groups can be used, use of an aminal, also known as an amidine or formamide, has the added benefit of rendering the molecule more soluble in organic solvents so as to allow the subsequent reactions to proceed more readily. To produce an aminal, the compound of formula (II) is reacted with a dialkyl acetal of a formamide of formula $Alk_2NCHO$. Acetal reactants thus include those of the formula $Alk_2NCH(OAlk)_2$ wherein Alk is independently alkyl, in particular of about 1 to 6 carbons. Other amine protection includes urethanes which can be produced by reaction of the amine with a chloroformate e.g. of formula $ClCOOCH_2CH_3$. Reaction with the amine protecting group reagent can be at about 25° to 100° C. in an organic solvent such as methanol, benzene or dimethylformamide.

as potassium hydroxide, sodium hydroxide, sodium methoxide and the like or pyridine and triethylamine and the like in protic solvents such as water, methanol, ethanol and the like. The amine protecting group (Pro=$CNMe_2$) can also be removed by hydride reduction with metal hydrides such as sodium borohydride and the like in protic solvents such as water, methanol, ethanol and the like. Under especially mild hydride reduction conditions, (Vp) with the amine protecting group Pro=$CNMe_2$ can be converted to (Vp) with the amine protecting group Pro=H, CHO as well as (V).

From formula (IIp), the compound of formula (IVp) is then produced by an oxidation, in particular via a Swern oxidation through the unstable intermediate (IIIp). When the alcohol function of (IIp) becomes an Reaction Scheme I

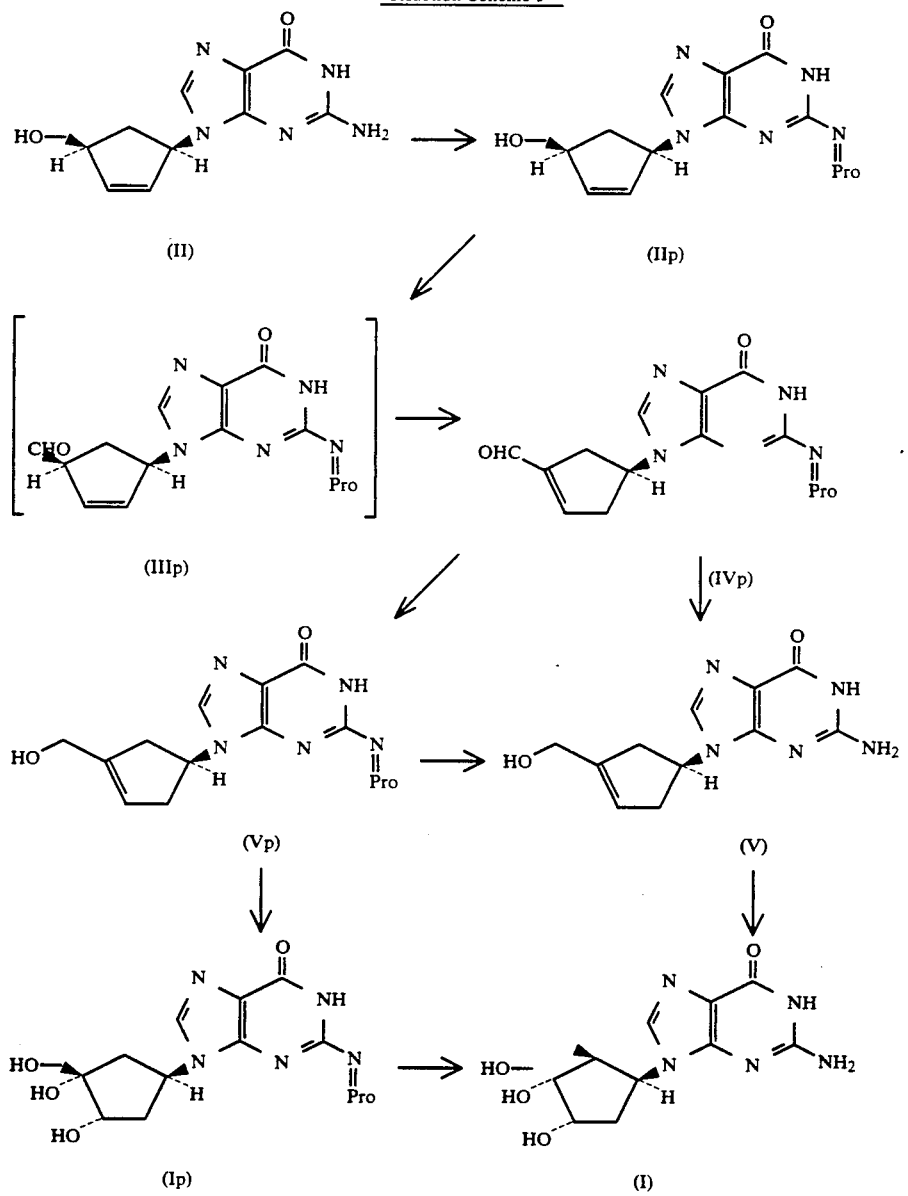

Removal of the amine protecting group can be carried out by techniques including acid- or base-catalyzed hydrolyses or hydride reduction. In more detail the hydrolyses can be carried out with acids such as hydrochloric acid and sulfuric acid and the like or bases such aldehyde, the double bond in (IIIp) spontaneously migrates to be in conjugation with the carbonyl of the aldehyde. Conditions for a Swern oxidation are generally excess molar equivalent amounts of oxalyl chloride, DMSO and triethylamine and a temperature of about −78° to +25° C. A review of the Swern oxidation is found in the article by A. J. Mancuso and Daniel Swern in Synthesis, pp 165–185, March 1981.

The compound of formula (IVp) is then either reduced to the corresponding alcohol (Vp) or reduced and deprotected simultaneously to yield (V). In the reduction to (Vp), an alkal metal borohydride, such as $NaBH_4$ or $NaBH_3CN$ may be used in an alcohol such as methanol at about −10° to 0° C., e.g. with 0.25 molar equivalents of $NaBH_4$ or 1.5 molar equivalents of $NaBH_3CN$. If the reduced and deprotected product (V) is desired directly, the reduction may be carried out with $NaBH_4$ in ethanol or a higher alcohol in an amount of at least 1 equivalent at about 0° to 25° C.

The compound of formula (Vp) and the compound of formula (V) may then be specifically 1,2-cis-hydroxylated with a catalyst such as osmium tetroxide ($OsO_4$) and an oxygen source. Reviews of osmium tetroxide oxidations include those of Martin Schroder in Chemical Reviews, 1980, 80, pp 187–213 and V. VanRheenen in Tetrahedron Letters, No. 23 pp. 1973–1976. In general, the reaction of (Vp) to (Ip) or (V) to (I) may be conducted in an $H_2O$: acetone mixture having a ratio of 1:1 to 50:1, at about 0° to 100° C., e.g. room temperature, with about 0.008 to 1 equivalent osmium tetroxide and an oxygen source such as hydrogen peroxide, N-methylmorpholine N-oxide, a metal chlorate, t-butyl hydroperoxide, sodium peroidate, oxygen gas or sodium hypochlorite.

Also part of the present invention are novel intermediates, e.g. of formulae (Ip), (IIp), (IIIp), (IVp), (Vp) and all enantiomers and diastereomers thereof and the (1'R)-and (1'S)-enantiomers of (V).

Further parts of the present invention include triols of formula (I) in the form of the i) hydrochloride, ii) hydrochloride monohydrate, and iii) hemihydrochloride monohydrate. The hydrochloride monohydrate is particularly important since it has a relatively lower melting point than other salts, is not hydroscopic and becomes increasingly pure through repeated recrystallizations and is thus suitable for use as an active ingredient in a formulated pharmaceutical. Another aspect of the invention is a method of removing osmium contamination from a nucleoside which comprises:

a) dissolving said nucleoside in a solvent to form a solution,
b) contacting said solution with a precipitating agent,
c) precipitating an osmium-containing residue from the solution, and
d) removing said residue from said solution.

In particular, the precipitating agent may be hydrogen sulfide, an aromatic pi base such as a pyridine, e.g. pyridine itself or a methyl mono-, di- or tri-substituted pyridine, or a mineral acid such as hydrochloric acid. Particular combinations of these precipitating agents are effective such as hydrogen sulfide, pyridine and water followed by hydrogen sulfide, hydrochloric acid and water over a period of up to 7 days.

In the following Examples and throughout the specification, the following abbreviations may be used: mg (milligrams); g (grams); ml (milliliters); hr (hours); min (minutes); mp (melting point); mmole (millimoles); MeOH (methanol); ICP-AA (Inductively Coupled Plasma-Atomic Absorption); and DMSO (dimethyl sulfoxide). Unless otherwise noted, all temperatures are expressed in ° C. (degrees centigrade).

EXAMPLE 1 a.

(1'R-cis)-2-Amino-1,9-dihydro-9-[4-(hydroxymethyl)-2-cyclopenten-1-yl]-6H-purin-6-one Dimethylaminal (Formula (IIp))

A 250 ml round-bottomed flask equipped with a condenser connected to a gas inlet was charged with 11.61 g (0.047 mole) of (1'R-cis)-2-amino-1,9-dihydro-9-[4-(hydroxymethyl)-2-cyclopenten-1-yl]-6H-purin-6-one of formula (II) and 110 ml of methanol under a nitrogen atmosphere. The mixture was heated to 65° C. and 9.8 ml (8.39 g, 0.070 mole) of dimethylformamide dimethylacetal was added. The mixture was heated to reflux and an additional 3.2 ml (2.74 g, 0.023 mole) of dimethylformamide dimethylacetal was added. The mixture was heated for 20 min at reflux, cooled to room temperature, and concentrated under vacuum to a 30 ml volume. A total of 110 ml of diethyl ether was added and the crystalline slurry was stirred briefly. The mixture was filtered and the crystalline solid was washed with 30 ml of diethyl ether. The product was dried under vacuum to constant weight to yield 13.27 g of (1'R-cis)-2-amino-1,9-dihydro-9-[4-hydroxymethyl)-2-cyclopenten-1-yl]-6H-purin-6-one dimethylaminal as a white solid, mp 211°–213° C.;$[\alpha]_D^{22}$ −170° (c 0.21, MeOH).

b.

(1'S)-2-Amino-1,9-dihydro-9-[4-formyl-3-cyclopenten-1-yl]-6H-purin-6-one Dimethylaminal (Formula (IVp))

A 5 ml flask fitted with a gas inlet and a rubber septum was charged with 0.050 g (0.0004 mole) of oxalyl chloride and 1.0 ml of methylene chloride and the solution was cooled to −48° C. under a nitrogen atmosphere. A solution of 0.056 ml (0.062 g, 0.0008 mole) of dimethyl sulfoxide in 0.050 ml of methylene chloride was added to the mixture via a syringe and the mixture was stirred at −48° C. for 5 minutes. A solution of 0.10 g (0.0003 mole) of (1'R-cis)-2-amino-1,9-dihydro-9-[4-(hydroxymethyl)-2-cyclopenten-1-yl]-6H-purin-6-one dimethylaminal, the product of Example 1a., in 0.60 ml of a 1:1 mixture of dimethyl sulfoxide-methylene chloride was added via syringe and this mixture was stirred at −48° C. for 10 minutes. The mixture was then allowed to warm to −18° C. and 0.275 ml (0.0020 mole) of triethylamine was added via syringe. The mixture was stirred at −18° C. for 10 minutes then allowed to warm to 0° C. and stirred for 1 hr. During this time, the initially formed (1'R-cis)-2-amino-1,9-dihydro-9-[4-formyl-2-cyclopenten-1-yl]-6H-purin-6-one dimethylaminal of formula (IIIp) underwent base-catalyzed double bond migration. The mixture was poured into 25 ml of saturated aqueous sodium bicarbonate solution and this mixture was extracted three times with 25 ml portions of methylene chloride. The combined organic layers were dried over 1.0 g of anhydrous magnesium sulfate, filtered, and concentrated under vacuum to yield 0.148 g of an oil. Purification of the oil by flash column chromatography on 40–63 μm silica gel and eluting with 9:1 chloroform:methanol provided 0.082 g of (1'S)-2-amino-1,9-dihydro-9-[4-formyl-3-cyclopenten-1-yl]-6H-purin-one dimethylaminal as a foam, $[\alpha]_D^{22}$+26° (c 0.41, $CHCl_3$).

c.
(1'S)-2-Amino-1,9-dihydro-9-[4-(hydroxymethyl)-3-cyclopenten-1-yl]-6H-purin-6-one Dimethylaminal (Formula (Vp)) and
(1'S)-2-Amino-1,9-dihydro-9-[4-(hydroxymethyl)-3-cyclopenten-1-yl]-6H-purin-6-one (Formula (V))

In a 25 ml flask was placed 0.223 g (0.00074 mole) of (1'S)-2-amino-1,9-dihydro-9-[4-formyl-3-cyclopenten-1-yl]-6H-purin-6-one dimethylaminal of Example 1b. dissolved in 10 ml of absolute ethanol and the mixture was cooled to 0° C. A total of 0.028 g (0.00074 mole) of sodium borohydride dissolved in 2 ml of absolute ethanol was added dropwise via syringe and the mixture was stirred at 0° C. for 25 minutes. The mixture was then quenched with 1.0 ml of water followed by stirring for 30 minutes at room temperature. The reaction mixture was mixed with 3 g of 230-400 mesh silica gel and concentrated to near dryness under vacuum. The resulting solid was added to a column of 8 g of silica gel. Purification by column chromatography via elution with 9:1 chloroform-methanol yielded 0.137 g of the less polar (1'S)-2-amino-1,9-dihydro-9-[4-(hydroxymethyl)-3-cyclopenten-1-yl]-6H-purin-6-one dimethylaminal, as a white foam: NMR (200 MHz, CDCl$_3$) δ9.4 (s, 1H), 8.6 (s, 1H), 7.7 (s, 1H), 5.7 (s, 2H), 5.2 (m, 1H), 4.3 (s, 2H), 3.2 (s, 3H), 3.1 (s, 3H) and 3.2-2.4 ppm (m, 4H). The column also yielded 0.048 g of the more polar (1'R-cis)-2-amino-1,9-dihydro-9-[4-(hydroxymethyl)-3-cyclopenten-1-yl]-6H-purin-6-one as a white foam: NMR (200 MHz, $^6$d-DMSO) δ10.5 (s, 1H), 7.6 (s, 1H), 6.5 (s, 2H), 5.6 (s, 1H), 4.9 (m, 1H), 4.8 (t, J=6Hz, 1H), 4.0 (d, J=6Hz, 2H), 2.8 (m, 2H) and 2.5 ppm (m, 2H).

d.
(1'S)-2-Amino-1,9-dihydro-9-[4-(hydroxymethyl)-3-cyclopenten-1-yl]-6H-purin-6-one Formamide (Formula (Vp)

A 100 mL round-bottomed flask containing 34 mL of deionized water, 0.09 mL (0.00112 mole) of 36% aqueous hydrochloric acid and 3.40 g (0.0112 mole) of (1'S)-2-amino-1,9-dihydro-9-[4-(hydroxymethyl)-3-cyclopenten-1-yl]-6H-purin-6-one dimethylaminal of example 1c. was placed in an oil bath preheated to 68° C. and stirred at this temperature for 45 min. An additional 0.84 mL (0.0101 mole) of 36% aqueous hydrochloric acid was added to the 68° C. solution, and stirring was continued for an additional 35 min. The solution was cooled to 23° C. and the pH was adjusted to pH 7 with 11.2 mL of 1N aqueous sodium hydroxide. Crystallization occurred immediately. To complete the crystallization, the slurry was cooled to 0° C. The dark colored solid was collected by vacuum filtration. The solid was washed with 150 mL of 1:1 ethanol-acetonitrile, then dried at 23° C. (0.5 mm) for 5 hr. The resulting 2.1 g of tan solid was dissolved in 250 mL of 1:1 methanol-deionized water at 65° C. The warm solution was treated with 2 g of Darco G-60 carbon, then hot-filtered through a ½ inch bed of diatomaceous earth. Crystallization occured in the filtrate during the filtration. To complete the crystallization, the filtrate was cooled to 0° C. The solids were collected by vacuum filtration and dried at 23° C. (0.5 mm) for 12 hr yielding 1.8 g of (1'S)-2-amino-1,9-dihydro-9-[4-(hydroxymethyl)-3-cyclopenten-1-yl]-6H-purin-6-one formamide as a white solid contaminated with approximately 20% of (1'S)-2-amino-1,9-dihydro-9-[4-(hydroxymethyl)-3-cyclopenten-1-yl]-6H-purin-6-one, mp 230°-245° C. (decomposed). A 1.12 g sample of this solid was triturated with 50 mL methanol at 60° C. The solids were collected by vacuum filtration and dried at 23° C. (0.5 mm) for 5 hr to provide 0.80 g of pure (1'S)-2-amino-1,9-dihydro-9-[4-(hydroxymethyl)-3-cyclopenten-1-yl]-6H-purin-6-one formamide as a white solid, mp 247°-250° C. (decomposed);[α]$_D^{22}$+14.1 (c 0.21, DMF).

$^1$H-NMR (200 MHz, $^6$d-DMSO) δ8.0 (s, 1H), 5.6 (s, 1H), 5.1 (m, 1H), 4.9 (bt, 1H), 4.1 (bs, 2H), 2.9 (m, 2H) and 2.6 ppm (m, 2H).

e. (1'S, 3'S, 4'S)-2-Amino-1,9-dihydro-9-[3,4-dihydroxy-3-(hydroxymethyl)-1-cyclopentanyl[-6H-purin-6-one Dimethylaminal (Formula (Ip))

A 500 ml 3-necked round-bottomed flask fitted with a condenser, and a gas inlet tube was charged with 2.70 g (0.0089 mole) of (1'S-cis)-2-amino-1,9-dihydro-[4-(hydroxymethyl)-3-cyclopenten-1-yl]-6H-purin-6-one dimethylaminal of formula (Vp), a product of Example 1c., 2.09 g (0.0179 mole) of 97% N-methylmorpholine N-oxide, 115 ml of deionized water and 1 ml of acetone. The reaction mixture was placed in an oil bath preheated to 70° C. and aqueous osmium tetroxide (4% w/w, 8.2 ml, 1.34 mmol) was added dropwise over 1 min. The mixture was stirred at 70° C. for 2 hr. The mixture was cooled to 0° C. and the mixture was quenched by adding 0.46 g (0.0044 mole) of sodium bisulfite and stirring for 20 minutes. The heterogeneous mixture was filtered and the solids were triturated twice with 30 ml portions of methanol and filtered. The combined filtrates were concentrated to dryness and residual water was removed under vacuum with an acetonitrile azeotrope. The solids were triturated twice with 50 ml portions of ether and filtered. These filtrates were evaporated to dryness to yield 4.57 g of solid. This material was slurried with 40 ml of methanol and 6 g of silica gel and the heterogeneous mixture was evaporated to dryness. The solid was placed on top of a 10 g column of silica gel and the column was eluted with 97:3→75:25 chloroform:methanol. The desired fractions were combined and evaporated to dryness to yield 2.25 g of solid. This material was dissolved in 15 ml of hot water, filtered and cooled to 0° C. to induce crystallization. Isolation of the product afforded 1.65 g of (1'S, 3'S, 4'S)-2-amino-1,9-dihydro-9-[3,4-dihydroxy-3-(hydroxymethyl)-1-cyclopentanyl]-6H-purin-6-one dimethylaminal as a white solid, mp 263°-268° C. (decomposed);[α]$_D^{22}$+77.6 (c 0.14, MeOH).

f. (1'S, 3'S, 4'S)-2-Amino-1,9-dihydro-9-[3,4-dihydroxy-3-(hydroxymethyl)-1-cyclopentanyl]-6H-purin-6-one anhydrous Hydrochloride Salt (Formula (I))

In a 50 ml flask was placed 1.48 g (0.0044 mole) of (1'S, 3'S, 4'S)-2-amino-1,9-dihydro-9-[3,4-dihydroxy-3-(hydroxymethyl)-1-cyclopentanyl]-6H-purin-6-one dimethylaminal, the product of Example 1e., the 7.5 ml of deionized water and 1.1 ml of concentrated hydrochloric acid and the mixture was stirred at 50° C. for 45 minutes under a nitrogen atmosphere. The hot solution was filtered and the filtrate was concentrated to 4 ml under vacuum. A total of 15 ml of absolute ethanol was added and the mixture was heated until homogeneous with the addition of 5 ml of absolute ethanol. The mixture was slowly cooled to room temperature, stirred for 2 hr and an additional 4 ml of absolute ethanol was added to fully induce crystallization. The solids were isolated by filtration and dried at 100° C. (0.2 mm) for 12 hours to yield 1.05 g of (1'S, 3'S, 4'S)-2-amino-1,9-dihydro-9-[3,4-dihydroxy-3-(hydroxymethyl)-1-cyclopentanyl]-6H-purin-6-one anhydrous hydrochloride salt as a hydroscopic white solid, mp 229°–230° C. (decomposed); $[\alpha]_D^{22}+14.5°$ (c 0.11, H$_2$O); residual osmium was 50 ppm by ICP-AA.

g. (1'S, 3'S, 4'S)-2-Amino-1,9-dihydro-9-[3,4-dihydroxy-3-(hydroxymethyl)-1-cyclopentanyl]-6H-purin-6-one (Formula (I))

A mixture of 0.273 g (0.00086 mole) of (1'S, 3'S,4'S)-2-amino-1,9-dihydro-9-[3,4-dihydroxy-3-(hydroxymethyl)-1-cyclopentanyl]-6H-purin -6-one hydrochloride, 2 ml of deionized water and 0.86 ml of 1N aqueous sodium hydroxide was heated to induce homogeneity under a nitrogen atmosphere. The solution was cooled to room temperature to induce crystallization and the solid was isolated in two crops. The solids were collected by filtration and were dissolved in 80 ml of hot methanol. The hot solution was filtered and concentrated to ca. 10 ml to induce crystallization. The 0.170 g of (1'S, 3'S, 4'S)-2-amino-1,9-dihydro-9-[3,4-dihydroxy-3-(hydroxymethyl)-1-cyclopentanyl]-6H-purin-6-one free base was obtained in two crops as an off-white solid, mp>280° C. (decomposed); $[\alpha]_D^{22}+13.3°$ (c 0.17, H$_2$O).

h. (1'S, 3'S, 4'S)-2-Amino-1,9-dihydro-9-[3,4-dihydroxy-3-(hydroxymethyl)-1-cyclopentanyl]-6H-purin-6-one Sodium Salt (Formula (I))

1. A mixture of 0.78 g (0.0025 mole) of (1'S, 3'S, 4'S)-2-Amino-1,9-dihydro-9-3,4-dihydroxy-3-(hydroxymethyl)-1-cyclopentanyl]-6H-purin-6-one hydrochloride salt, 5 ml of deionized water and, 0.245 g (0.0061 mole) of sodium hydroxide dissolved in 0.5 ml of deionized water was stirred at room temperature for 5 minutes. An additional 5 ml of deionized water was added and followed by enough absolute ethanol to produce a cloudy solution. The mixture was heated until homogeneous then cooled to room temperature to produce an oily two-phased solution. The mixture was evaporated to dryness under vacuum using an acetonitrile azeotrope. The remaining oil was triturated with 80 ml of hot methanol. The residual solid salts were removed by filtration. The mixture was concentrated to 15 ml and acetonitrile was added to the cloud point. The mixture was heated to induce homogeneity, then was cooled to room temperature to induce crystallization. The solid first crop was collected and the filtrate was concentrated to half volume and an equal volume of hot ethanol was added to induce a second crop of crystals. The combined crops were dissolved in hot methanol, concentrated to 15 ml and stirred at room temperature to produce 0.420 g of (1'S, 3'S, 4'S)-2-amino-1,9-dihydro-9-[3,4-dihydroxy-3-(hydroxymethyl)-1-cyclopentanyl]-6H-purin-6-one sodium salt as a white solid, mp>265° C.; $[\alpha]_D^{22}+6.6°$ (c 0.24, H$_2$O).

2. A solution of 0.491 g (0.0123 mole) of sodium hydroxide in 250 ml of methanol was heated to 64° C. The hot solution was added to a 500 ml round-bottomed flask containing 3.90 g (0.0123 mole) of 98+% pure (1'S, 3'S, 4'S)-2-amino-1,9-dihydro-9-[3,4-dihydroxy-3-(hydroxymethyl)-1-cyclopentanyl]-6H-purin-6-one. The white solids went into solution for a moment, then immediately precipitated out as a white, free flowing powder. The slurry was stirred for 30 minutes and allowed to cool to room temperature. The solvent volume was reduced to 35 ml in vacuo, and 60 ml of diethyl ether was added at once. The slurry was stirred for 30 minutes and the white precipitate was collected by vacuum filtration under a blanket of nitrogen. The resulting hydroscopic solid was dried in vacuo (0.5 mm, 65° C., 24 h) to provide 3.72 g of (1'S, 3'S, 4'S)-2-amino-1,9-dihydro-9-[3,4-dihydroxy-3-(hydroxymethyl)-1-cyclopentanyl]-6H-purin-6-one sodium salt, mp>278° C. (decomposed), $[\alpha]_D^{22}+9.86°$ (c 0.21, H$_2$O); residual osmium was 1.6 ppm by ICP-AA.

EXAMPLE 2 a. (1'S)-2-Amino-1,9-dihydro-9-[4-(hydroxymethyl)-3-cyclopenten-1-yl]-6H-6-one Dimethylaminal (Formula (Vp))

The following Example represents a combination of the procedures of Examples of 1b and 1c with isolation of a single product.

A 1 L four-necked, round-bottomed flask fitted with a mechanical stirrer, a gas inlet tube, a thermometer, and a pressure-equalized dropping funnel and a rubber septum was charged with 200 ml of methylene chloride under a nitrogen atmosphere and the solution was cooled to −48° C. A total of 4.0 ml (5.35 g, 0.041 mole) of oxalyl chloride was added directly to the solution by syringe. The addition funnel was charged with 11.8 ml of a 1:1 mixture of dimethyl sulfoxide and methylene chloride and this solution was added dropwise to the reaction mixture at a rate such that the temperature remained below −35° C. The solution was stirred for 5 minutes as the mixture was recooled to −48° C. The addition funnel was changed with 10.0 g (0.033 mole) of (1'R-cis)-2-amino-1,9-dihydro-9-[4-(hydroxymethyl)-2-cyclopenten-1-yl]-6H-purin-6-one dimethylaminal of formula (IIp), in 100 ml of 1:1 dimethyl sulfoxide:methylene chloride. This solution was added to the reaction mixture over a 15 minute period. The reaction mixture was then stirred at −48° C. for 5 minutes, then 21.0 ml (0.015 mole) of triethylamine dissolved in 21.0 ml of methylene chloride was added dropwise over a 4 minute period. The reaction mixture was warmed in an ice-water bath to 0° C. and stirred at 0° C. for 2.5 hr. The reaction mixture was then poured into 200 ml of saturated aqueous sodium bicarbonate solution and this mixture was extracted three times with 150 ml portions of methylene chloride. The combined organic extracts were dried over 10.0 g of anhydrous magnesium sulfate, filtered and concentrated under vacuum to a volume of 30 ml which contained crude (1'S)-2-amino-1,9-dihydro-9-[4-formyl-3-cyclopenten-1-yl]-6H-purin-6-one dimethylaminal. This concentrate was diluted with 30 ml of methanol and cooled to 0° C. A solution of 0.63 g (0.017 mole) of sodium borohydride in 15 ml of absolute ethanol was added dropwise over 3 minutes. The mixture was stirred at 0° C. for 25 minutes and excess sodium borohydride was quenched by the addition of 1.0 ml of water. The solution was mixed with 30.0 g of 230–400 mesh silica gel and evaporated under vacuum to near dryness. The resulting solid was added to a column of 80.0 g of 230–400 mesh silica gel. Purification by column chromatography via elution with 95:5→85:15 chloroform:methanol afforded 6.77 g of (1'S)-2-amino-1,9-dihydro-9-[4-(hydroxymethyl)-3-cyclopenten-1-yl]-6H-purin-6-one dimethylaminal as a white solid mp 108°-110° C.-solidified and remelted at 194°-195° C.; $[\alpha]_D^{22}$ −10.2° (c 0.19, MeOH).

b. (1'S, 3'S, 4'S)-2-Amino-1,9-dihydro-9 [3,4-dihydroxy-3-(hydroxymethyl)-1-cyclopentanyl]-6H-purin-6-one Dimethylaminal (Formula (Ip))

A 500 ml, four-necked round-bottomed flask equipped with an air-driven stirrer, a reflux condenser and a nitrogen/thermometer inlet was charged with 20.0 g (0.0662 mole) of (1'S)-2-amino-1,9-dihydro-9-[4-(hydroxymethyl)-3-cyclopenten-1-yl]-6H-purin-6-one dimethylaminal of formula (Vp), 15.5 g (0.128 mole) of N-methylmorpholine-N-oxide, 240 ml of deionized water and 48 ml of acetone. The slurry became a homogeneous solution as it was heated to 70° C. under a nitrogen atmosphere. To the solution was added 10 ml (1.6 mmol) of aqueous osmium tetroxide (4% wt/wt) via syringe. The solution was stirred at 70° C. for 1 hour and cooled to 10° C. The dark green solution was vacuum filtered and the filtrate was concentrated in vacuo to a dark colored semisolid. The dark solid was triturated with 1.0 L of methanol at 60° C., then filtered. This trituration process was repeated twice. The combined filtrates were concentrated in vacuo to give 30.2 g of a brown solid. Purification by flash chromatography (300 g of 40-63 μm silica gel using chloroform/methanol/acetic acid, 9:1:0.1 to 4:1:0.1) provided an oil which solidified upon trituration with 2×250 ml toluene. The resulting solids were dried in vacuo (0.5 mm, 63° C., 12 hr) to give 18.9 g, of (1'S, 3'S, 4'S)-2-amino-1,9-dihydro-9-[3,4-dihydroxy-3-(hydroxymethyl)-1-cyclopentanyl]-6H-purin-6-one dimethylaminal in 85% yield as a white solid, mp 234°-236° C. (dec); $[\alpha]_D^{22}$ +68° (c 0.05, methanol).

c. (1'S, 3'S, 4'S)-2-Amino-1,9-dihydro-9-[3,4-dihydroxy-3-(hydroxymethyl)-1-cyclopentanyl]-6H-purin-6-one Hydrate (Formula (I))

A 3 liter, four-necked round-bottomed flask equipped with an air driven stirrer, a thermostat-controlled heating mantle, a reflux condenser vented through a bleach trap and a fine fritted gas inlet tube was charged with 42.7 g (0.127 mole) of (1'S, 3'S, 4'S)-2-amino-1,9-dihydro-9-[3,4-dihydroxy-3-(hydroxymethyl)-1-cyclopentanyl]-6H-purin-6-one dimethylaminal of Formula (Ip) and 1.14 L of deionized water. The slurry was heated with stirring to 65° C. to form a homogeneous solution, then hydrogen sulfide gas was gently bubbled into the solution for 2 hours to precipitate osmium containing impurities. The gas inlet tube was removed, the condenser was connected to a nitrogen atmosphere and the reaction mixture was stirred at 65° C. After 22 hours, 600 ml of absolute ethanol was added to the warm reaction mixture and the solution was hot-filtered through a 2 inch pad (100 g) of diatomaceous earth in a hot, steam-jacketed filter funnel. The pad was washed with 500 mL of 1:1 ethanol-water. The combined filtrates were cooled to 25° C., then to 0° C. over 1.5 hr to induce crystallization. The crystals were collected by vacuum filtration. The filtrate volume was reduced in vacuo to 150 ml and a second crop of crystals was collected by vacuum filtration. The damp 47.0 g of first and second crops were combined with 1.95 L of 60:40 methanol-deionized water in a 3 L four-necked round-bottomed flask equipped with an air-driven stirrer, a reflux condenser vented to a bleach bath, a thermometer, and a fine fritted gas inlet tube. The solution was heated to 60° C. and hydrogen sulfide was gently bubbled into the stirred solution for 30 seconds. The solution was stirred for 30 minutes at 60° C., then hot filtered through a 2 inch pad (100 g) of diatomaceous earth in a hot, steam-jacketed filter funnel. The pad was washed with 250 ml of 1:1 ethanol:deionized water. The filtrate volume was reduced in vacuo to 550 ml, then cooled to 0° C. to induce crystallization. The crystals were collected by vacuum filtration. The crystals were washed with 250 ml of absolute ethanol, then 350 ml of 9:1 acetonitrile-ethanol to assist in drying. The crystals were transferred to 500 ml round-bottomed flask and dried in vacuo (0.5 mm, 25° C., 5 hours) to provide 32.2 g of (1'S, 3'S, 4'S)-2-amino-1,9-dihydro-9-[3,4-dihydroxy-3-(hydroxymethyl)-1-cyclopentanyl]-6H-purin-6-one hydrate in 90% yield.

NMR (200 MHz, $^6$d-DMSO) δ10.6 (s, 1H), 7.8 (s, 1H), 6.4 (s, 2H), 4.9 (m, 1H), 4.8 (m, 2H), 4.3 (s, 1H), 4.2 (t, J=6Hz, 1H), 3.4 (m, 2H) and 2.1 ppm (m, 4H).

d. (1'S, 3'S, 4'S)-2-Amino-1,9-dihydro-9-[3,4-dihydroxy-3-(hydroxymethy)-1-cyclopentanyl]-6H-purin-6-one Hydrate (formula(I))

The following Example represents a combination of the procedure of Example 2b and 2c with isolation of a single product.

A 5 L four-necked, round-bottomed flask equipped with an air driven stirrer, a reflux condenser vented to a bleach trap, a fine fritted gas inlet tube and thermometer was charged with 2.4 L of deionized water and 0.6 L of acetone, then heated to 70° C. To the 70° C. solution was added 72.6 g (0.620 mole) of N-methylmorpholine N-oxide and 75.0 g (0.248 mole) of (1'S)-2-amino-1,9-dihydro-9-[4-(hydroxymethyl)-3-cyclopenten-1-yl]-6H-purin-6-one dimethylaminal of formula (Vp) followed by 1.0 g (0.0039 mole) of osmium tetroxide. The solution was stirred at 70° C. for 35 minutes, and 500 ml of pyridine was added. The solution was saturated with hydrogen sulfide gas and stirred at 70° C. for 96 hr to reduce osmate esters and remove colloidal osmium containing impurities. The solution was resaturated with hydrogen sulfide every 24 hr. Activated carbon (20 g, Darco G 60) was added to the reaction mixture to remove precipitated osmium containing impurities and elemental sulfur. The hot solution was vacuum filtered through filter paper and the filtrate was concentrated in situ to a dark colored, viscous slurry of about 75 ml. The semi-solid slurry was diluted with 700 mL of acetonitrile at 23° C. and this slurry was stirred for 12 hr. The resulting solids were collected by vacuum filtration to yield 76 g of damp material. The tan colored solids were dissolved in 2.6 L of deionized water at 80° C. To maintain solubility, 700 mL of absolute ethanol was added to the 80° C. solution. This hot, homogeneous solution was decolorized with 20 g of activated carbon (Darco G 60) then hot filtered through a 1 inch bed (100 g) of diatomaceous earth in a steam jacketed filter funnel. The filtrate volume was reduced to 1.5 L by vacuum distillation to initiate crystallization. The slurry was stirred for 12 hr at 23° C., then 2 hr at 0° C. to fully effect crystallization. The solids were collected by vacuum distillation to initiate crystallization. The solids were collected by vacuum filtration, washed with 200 ml of absolute ethanol then dried in vacuo (0.5 mm, 23° C., 12 hr) to provide 54.0 g of (1'S, 3'S, 4'S)-2-amino-1,9-dihydro-9-[3,4-dihydroxy-3-(hydroxymethyl)-1-cyclopentanyl]-6H-purin-6-one hydrate as a white solid containing 8.4 ppm residual osmium as determined by ICP-AA. A 5 L four-necked, round-bottomed flask equipped as previously described was charged with 1.2 L of deionized water, 48.5 ml of 36% concentrated hydrochloric acid and 54.0 g of (1'S, 3'S, 4'S)-2-amino-1,9-dihydro-9-[3,4-dihydroxy-3-(hydroxymethyl)-1-cyclopentanyl]-6H-purin-6-one hydrate. The solution was heated to 70° C., saturated with hydrogen sulfide gas and stirred for 24 hr. The hot solution was vacuum filtered through Whatman P3 filter paper to remove osmium containing impurities and elemental sulphur. The filtrated was returned to a 5 L four-necked, round-bottomed flask equipped as previously described. The solution was heated to 80° C. and the solution was adjusted to pH 7 with about 40 mL of 30% aqueous ammonium hydroxide. To maintain solubility, 500 mL of ethanol was added to the 80° C. solution. The hot solution was decolorized with 20 g of activated carbon, then hot filtered through a 1 inch bed (10 g) of diatomaceous earth in a steam jacketed filter funnel. The filtrated volume was reduced in situ to 900 ml to effect crystallization. To complete the crystallization process, the slurry was stirred for 3 hr at 23° C., then 1 hr at 0° C. The solids were collected by vacuum filtration, washed with 100 mL of water at 0° C., 100 ml of 1:1 water/absoute ethanol at 0° C., then 100 ml of absolute ethanol at room temperature. The white crystals were dried in vacuo (0.5 mm, 65° C., 24 hr) to provide 46.3 g of (1'S, 3'S, 4'S)-2-amino-1,9-dihydro-9-[3,4-dihydroxy-3-(hydroxymethyl)-1-cyclopentanyl]-6H-purin-6-one hydrate in 66% yield, mp>199°-204° C. (decomposed), $[\alpha]_D^{22}+13°$ (c 0.17, $H_2O$), residual osmium was 0.8 ppm by ICP-AA.

EXAMPLE 3

(1'S, 3'S, 4'S)-2-Amino-1,9-dihydro-9-[3,4-dihydroxy-3-(hydroxymethyl)-1-cyclopentanyl]-6H-purin-6-one (Formula (I))

A 250 ml round-bottomed flask equipped with a magnetic stirrer and a reflux condenser vented through a nitrogen atmosphere was charged with 1.0 g (0.0040 mole) of (1'S)-2-amino-1,9-dihydro-9-[4-(hydroxymethyl)-3-cyclopenten-1-yl]-6H-purin-6-one of formula (V), 1.18 g (0.0101 mole) of N-methylmorpholine N-oxide, 32 ml of deionized water and 8 ml of acetone. The solution was placed in an oil bath preheated to 70° C., and 1.25 ml (0.000202 mole) of aqueous osmium tetroxide (4% wt/wt) was added by syringe over 1 minute. The color of the solution changed from pale yellow to deep amber after the addition. After stirring 50 minutes at 70° C., 2.1 g (0.0202 mole) of sodium bisulfite was added. The reaction mixture was stirred for 2 hours at 70° C., then vacuum filtered through 8 g of diatomaceous earth. The filtrate was transferred to a 250 ml round-bottomed flask and concentrated under vacuum. The resulting solids were triturated with 50 mL of 9:1 acetonitrile:ethanol. The liquid phase was decanted and the solids were dried in vacuo. The solids were then dissolved in 30 ml of deionized water at 70° C. and filtered. The filtrate was cooled to 0° C. to induce crystallization and the crystals were collected by vacuum filtration. The solids were washed with 50 ml of acetonitrile, transferred to a 100 ml round-bottomed flask and dried in vacuo (0.5 mm, 25° C., 12 hours) to provide 0.824 g of (1'S, 3'S, 4'S)-2-amino-1,9-dihydro-9-[3,4-dihydroxy-3-(hydroxymethyl)-1-cyclopentanyl]-6H-purin-6-one, mp>265° C., (decomposed); $[\alpha]_D^{22}+13.7°$ (c 0.07, MeOH); 336 ppm residual osmium by ICP-AA.

EXAMPLE 4

(1'S)-2-Amino-1,9-dihydro-9-[4-(hydroxymethyl)-3-cyclopenten-1-yl]-6H-purin-6-one (Formula (V))

A solution of 2.25 g (0.00744 mole) of (1'S)-2-amino-1,9-dihydro-9-[4-(hydroxymethyl)-3-cyclopenten-1-yl]-6H-purin-6-one dimethylaminal of formula (Vp), 8.3 ml (0.0083 mole) of 1N aqueous sodium hydroxide and 12 ml of deionized water was placed in 100 ml round-bottomed flask equipped with a magnetic stir bar and a reflux condenser. The solution was stirred for 30 minutes at 23° C., then warmed to 65° C. and stirred for 80 minutes. The solution was cooled to 23° C. and the pH was adjusted to pH7 with 0.5 ml of glacial acetic acid in 10 ml of deionized water to induce crystallization. The slurry was cooled to 0° C., and the crystals were collected by vacuum filtration. The damp, white crystals were washed with 10 ml of acetonitrile, transferred to a 100 ml round-bottomed flask and dried in vacuo (0.5 mm, 23° C., 12 hours) to provide 1.43 g of (1'S)-2-amino-1,9-dihydro-9-[4-(hydroxymethyl)-3-cyclopenten-1-yl]-6H-purin-6-one, mp 260°-265° C. (decomposed); $[\alpha]_D^{22}+12.5°$ (c 0.12, MeOH).

EXAMPLE 5

(1'S)-2-Amino-1,9-dihydro-9-[4-(hydroxymethyl)-3-cyclopenten-1-yl]-6H-purin-6-one Dimethylaminal (Formula (Vp))

A solution of 1.16 g (0.00386 mole) of (1'S)-2-amino-1,9-dihydro-9-[4-formyl-3-cyclopenten-1-yl]-6H-purin-6-one dimethylaminal of formula (IVp) in 25 ml of methanol was placed in a 100 ml round-bottomed flask equipped with a magnetic stir bar and a reflux condenser vented to a nitrogen atmosphere. The solution was cooled to −10° C. and 0.039 g (0.0010 mole) of powdered sodium borohydride was added at once. The solution was stirred for 20 minutes at −10° C. then concentrated in vacuo onto 1 g of 230–400 mesh silica gel. This solid was added to the top of a small column of 230–400 mesh silica gel and was chramotographed on a column of 230–400 mesh silica gel using 9:1 chloroform:methanol as eluant, provided 0.86 g of (1'S)-2-amino-1,9-dihydro-9-[4-(hydroxymethyl)-3-cyclopenten-1-yl]-6H-purin-6-one dimethylaminal as a white foam: NMR (200 MHz, $^6$d-DMSO) δ11.3 (s, 1H), 8.6 (s, 1H), 7.8 (s, 1H) 5.6 (s, 1H), 5.2 (m, 1H), 4.9 (t, J=6 Hz, 1H), 4.1 (d, J=6 Hz, 2H), 3.1 (s, 3H), 3.0 (s, 3H), 2.8 (m, 2H) and 2.5 ppm (m, 2H).

EXAMPLE 6

(1'S)-2-Amino-1,9-dihydro-9-[4-hydroxymethyl)-3-cyclopenten-1-yl]-6H-purin-6-one Hydrate (Formula (V))

A solution of 0.400 g (0.00133 mole) of (1'S)-2-amino-1,9-dihydro-9-[4-formyl-3-cyclopenten-1-yl]-6H-purin-6-one dimethylaminal of formula (IVp) in 15 ml of absolute ethanol was placed in a 100 ml round-bottomed flask equipped with a magnetic stir bar and a reflux condenser vented to a nitrogen atmosphere. The solution was cooled to 0° C. and 0.051 g (0.00133 mole) of powdered sodium borohydride was added at once. The solution was warmed to 23° C. and stirred for 3.5 hours. To the solution was added 0.11 ml (0.00133 mole) of 36% aqueous hydrochloric acid. The reaction was stirred for 30 minutes at 23° C., then concentrated in vacuo onto 2 g of 230–400 mesh silica gel. Purification by flash chromatography (4 g of 230–400 mesh silica gel, eluted with 4:1 chloroform:methanol) provided 0.32 g of (1'S)-2-amino-1,9-dihydro-9-[4-(hydroxymethyl)-3-cyclopenten-1-yl]-6H-purin-6-one as a glass-like solid. The solid was dissolved in 10 ml of hot ethanol and the volume was reduced to 4 ml in vacuo when crystals formed. To this mixture was added 25 ml of acetonitrile. The resulting slurry was cooled to 0° C., and the crystals were collected by vacuum filtration then dried in vacuo (0.5 mm, 23° C., 5 hours) to provide 0.24 g of (1'S)-2-amino-1,9-dihydro-9-[4-(hydroxymethyl)-3-cyclopenten-1-yl]-6H-purin-6-one hydrate as a white solid, mp 148°–160° C. (decomposed); $[\alpha]_D^{22}+14°$ (c 0.20, MeOH).

EXAMPLE 7

(1'S, 3'S, 4'S)-2-Amino-1,9-dihydro-9-[3,4-dihydroxy-3-(hydroxymethyl)-1-cyclopentanyl]-6H-purin-6-one Hydrochloride Monohydrate Salt (Formula (I))

A hydrochloric acid solution was prepared by charging an Erlenmeyer flask with 230 ml (2.76 moles) of concentrated hydrochloric acid (Baxter, Baker analyzed) and 645 ml of deionized water. The solution was stirred and cooled to 20°–25° C. A 5 L four-necked round-bottomed flask equipped with a glass rod air stirrer, a thermometer, a thermometer inlet, a condenser and a powder funnel was charged with 625 mL of the hydrochloric acid solution and 258.3 g (0.918 mole) of (1'S, 3'S, 4'S)-2-amino-1,9-dihydro-9-(3,4-dihydroxy-3-hydroxymethyll-1-cyclopentyl)-6H-purin-6-one of formula (I) was added. Another 50 ml of the hydrochloric acid solution was used to complete transfer. Complete solution occurred in 5–10 minutes following the addition. The solution was filtered through Whatman P4 filter paper to remove any insoluble particulate matter. The residual material was washed with 100 ml of the hydrochloric acid solution. The wash and filtrate were combined and returned to a clean 5 L four-necked round-bottomed flask equipped as previously described. Another 100 ml of the hydrochloric acid solution was used to complete the transfer. Then the solution was stirred at 20°–25° C. while adding 3.5 L of absolute ethanol over a 30-minute period to induce crystallization. Following completion of the alcohol addition, the white slurry was stirred for 30 minutes at 20°–25° C. Then the slurry was cooled to 0°–5° C. over a 30-minute period then was stirred at 0°–5° C. for 1 hr before isolating the product by filtration on Whatman P4 filter paper. The solids were washed with 2×125 ml=250 ml of absolute ethanol at 0°–5° C. The product was placed in a vacuum oven at 63° C. (1 mm) to dry to constant weight, providing 263.9 g of white crystalline (1'S, 3'S, 4'S)-2-amino-1,9-dihydro-9-[3,4-dihydroxy-3-(hydroxymethyl)-1-cyclopentanyl]-6H-purin-6-one hydrochloride monohydrate salt.

A 2 L Erlenmeyer flask equipped with magnetic stir bar was charged with 138.4 ml (1.66 moles) of 36% concentrated hydrochloric acid and 553 ml of deionized water. A 250 ml aliquot of this hydrochloric acid solution was retained for rinses. The hydrochloric acid solution was heated to 45° C. before adding 263.0 g (0.783 mole) (1'S, 3'S, 4'S)-2-amino-1,9-dihydro-9-[3,4-dihydroxy-3-(hydroxymethyl)-1-cyclopentanyl]-6H-purin-6-one hydrochloride monohydrate salt of formula (I). The material was rinsed in with 250 ml of hydrochloric acid solution to complete the transfer. Complete solution occurred in 5–10 minutes following the addition. The solution was heated to 65° C. and filtered through Whatman P4 filter paper to remove any particulate matter. The residual material was washed 2×50 ml=100 ml of deionized water. The wash and filtrate were combined and transferred to a 5 L four-necked round-bottomed flask equipped with a glass rod air stirrer, a thermometer inlet, a thermometer, a condenser and an addition funnel. The transfer was completed using 38 mL of deionized water. The solution was stirred at 50° C. while adding 3.5 L absolute ethanol over a 30-minute period to induce crystallization. The thick white slurry was stirred for 1 hr before isolating the product by filtration on Whatman P4 paper. The product was washed with 2×250 ml=500 ml of absolute ethanol at 0°–5° C. The product was dried in a vacuum oven at 63° C. (1 mm) to constant weight to provide 232.0 g of (1'S, 3'S, 4'S)-2-amino-1,9-dihydro-9-[3,4-dihydroxy-3-(hydroxymethyl)-1-cyclopentanyl]-6H-purin-6-one hydrochloride monohydrate salt as a white solid, mp 172°–179° C. (decomposed); $[\alpha]_D^{22}+15.8°$ (c 0.50, H$_2$O).

EXAMPLE 8

(1'S, 3'S, 4'S)-2-Amino-1,9-dihydro-9-]3,4-dihydroxy-3-(hydroxymethyl)-1-cyclopentanyl]-6H-purin-6-one Hemihydrochloride Monohydrate Salt (Formula (I))

A 2 L Erlenmeyer flask equipped with a magnetic stir bar was charged with 27 ml of deionized water and 9.0 g (0.027 mole) of (1'S, 3'S, 4'S)-2-amino-1,9-dihydro-9-[3,4-dihydroxy-3-(hydroxymethyl)-1-cyclopentanyl]-6H-purin-6-one hydrochloride monohydrate salt of formula (I). The slurry was heated to 65° C. and complete solution occured at 45° C. The hot solution was filtered through Whatman P4 filter paper to remove any insoluble particulate matter. Another 9 ml of deionized water was used to complete the transfer and wash the residue. The combined wash and filtrate were transferred to a 500 ml four-necked round-bottomed flask equipped with a glass rod air stirrer, a thermometer inlet, a thermometer, a condenser and an addition funnel. The hot solution was stirred and 130 ml of absolute ethanol was added over a 30-minute period. The slurry was stirred for 2 h while cooling to 20°–25° C., then was cooled with stirring to 0°–5° C. over a 30-minute period. The slurry was stirred for an additional 2 hr at 0°–5° C. before isolating the product by filtration. The solids were washed with 2×15 ml=30 ml of absolute ethanol at 0°–5° C. The product was dried in a vacuum oven at 63° C. to constant weight providing 7.0 g of (1'S, 3'S, 4'S)-2-amino-1,9-dihydro-9-[3,4-dihydroxy-3-(hydroxymethyl)-1-cyclopentanyl]-6H-purin-6-one hemihydrochloride monohydrate salt, mp 241°–243° C. (decomposed); $[\alpha]_D^{22}+14.7°$ (c 0.41, H$_2$O).

EXAMPLE 9

(1'S, 3'S, 4'S)-2-Amino-1,9-dihydro-9-[3,4-dihydroxy-3-(hydroxymethyl)-1-cyclopentanyl]-6H-purin-6-one Anhydrous Hydrochloride Salt (Formula (I))

A total of 1.24 g (0.0037 mole) of (1'S, 3'S, 4'S)-2-amino-1,9-dihydro-9-[3,4-dihydroxy-3-(hydroxymethyl)-1-cyclopentanyl]-6H-purin-6-one hydrochloride monohydrate salt of formula (I) was placed in an evaporating dish and dried in a vacuum oven (103° C., 0.5 mm) for 12 hr. The 1.16 g of the resulting hydroscopic solid was identified as (1'S, 3'S, 4'S)-2-amino-1,9-dihydro-9-[3,4-dihydroxy-3-(hydroxymethyl)-1-cyclopentanyl]-6H-purin-6-one anhydrous hydrochloride salt, mp 229°–230° C. (decomposed); $[\alpha]_D^{22}$ +16.2° (c 0.28, $H_2O$).

What is claimed is:

1. A method of synthesizing a triol of the following formula (Ip):

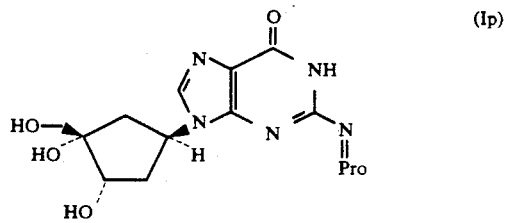

wherein Pro is an amino protecting group, which comprises the steps of:

i) oxidizing a cyclopentene of the following formula (IIp):

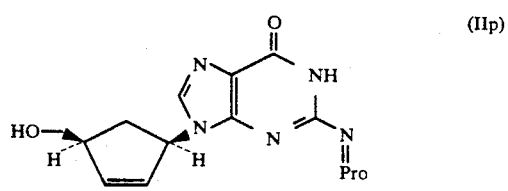

to yield an aldehyde of the following formula (IVp):

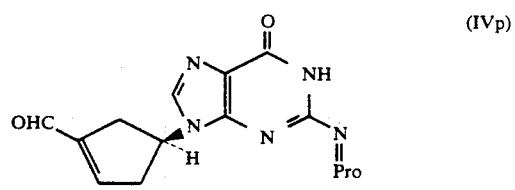

ii) reducing the aldehyde of formula (IVp) to yield the monoalcohol of the following formula (Vp):

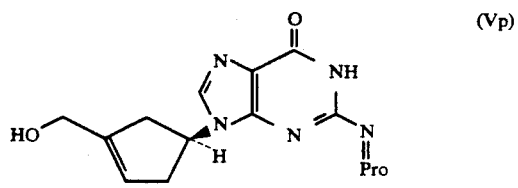

and iii) performing a cis-hydroxylation on the monoalcohol of formula (Vp) to produce the triol of formula (Ip).

2. The method of claim 1, wherein said oxidizing step i) is a Swern oxidation.

3. The method of claim 2, wherein said Swern oxidation is conducted with oxalyl chloride, dimethyl sulfoxide and triethylamine.

4. The method of claim 2, wherein said Swern oxidation is conducted at about −78° to +25° C.

5. The method of claim 1, wherein said reducing step ii) is conducted with an alkali metal borohydride.

6. The method of claim 5, wherein said reducing step ii) is conducted at about −10° to 0° C.

7. The method of claim 1, wherein said cis-hydroxylation step iii) is conducted with an osmium tetroxide catalyst and an oxygen source.

8. The method of claim 1, wherein said cis-hydroxylation step iii) is conducted at about 0° to 100° C.

9. The method of claim 1, further comprising the step of iv) deprotecting the triol (Ip) to yield the purine of the following formula (I):

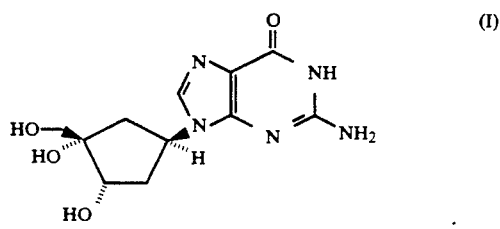

or an acid- or base-addition salt thereof.

10. A method of synthesizing the purine of the following formula (I):

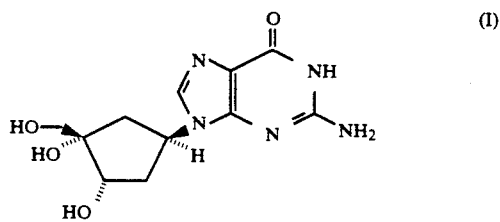

or an acid- or base-addition salt thereof, which comprises the steps of:

a) oxidizing a cyclopentene of the following formula (IIp):

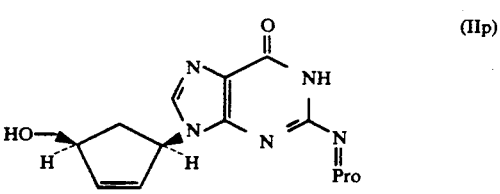

wherein Pro is an amine protecting group to yield an aldehyde of the following formula (IVp):

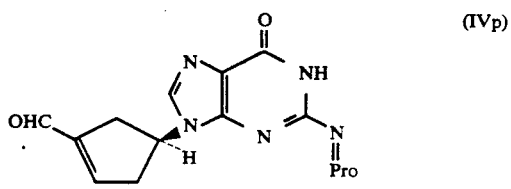

b) reducing the aldehyde of formula (IVp) to yield the monoalcohol of the following formula (Vp):

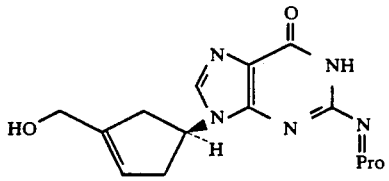

c) performing a cis-hydroxylation on the monoalcohol of formula (Vp) to produce the triol of the following formula (Ip):

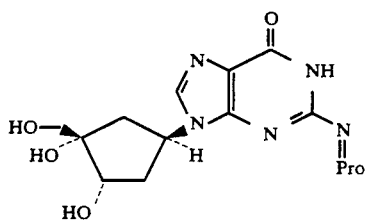

and d) deprotecting the triol of formula (Ip) to produce the purine of formula (I), or alternatively, in the place of steps b), c) and d), performing the following steps e) and f):

e) reducing the aldehyde of formula (IVp) to yield the alkenol of the following formula (V):

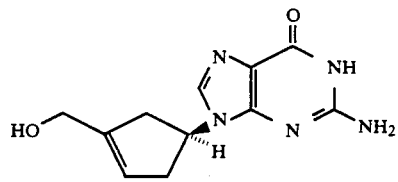

and f) performing a cis-hydroxylation on the alkenol of formula (V) to produce the purine of formula (I).

11. The method of claim 10, wherein said reducing step b) is conducted at about −10° to 0° C. with an alkali metal borohydride and said alternative reducing step e) is conducted at about 0° to 25° C. with an alkali metal borohydride.

12. A method of synthesizing an aldehyde of the following formula (IVp):

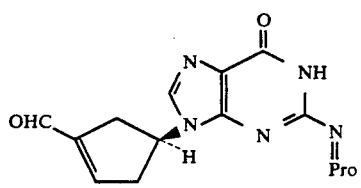

wherein Pro is an amine protecting group, which comprises the step of oxidizing a cyclopentene of the following formula (IIp):

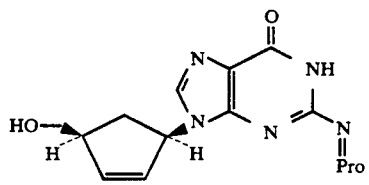

13. The method of claim 1, wherein Pro is an aminal protecting group.

* * * * *